United States Patent [19]
Buck et al.

[11] Patent Number: 5,171,212
[45] Date of Patent: Dec. 15, 1992

[54] BLOOD PUMPING SYSTEM WITH BACKFLOW WARNING

[75] Inventors: Greta L. Buck; Richard A. Nazarian, both of St. Paul, Minn.

[73] Assignee: Minnesota Mining and Manufacturing Company, St. Paul, Minn.

[21] Appl. No.: 652,510

[22] Filed: Feb. 8, 1991

[51] Int. Cl.$^5$ .................. A61M 1/03; F04B 49/00
[52] U.S. Cl. .................... 604/4; 604/67; 128/691; 417/20
[58] Field of Search .................. 604/4-6, 604/31, 50, 65-67, 118, 121; 128/691, 692, DIG. 3, 12; 210/87; 415/900; 417/18-27

[56] References Cited

U.S. PATENT DOCUMENTS

| | | | |
|---|---|---|---|
| 3,815,582 | 6/1974 | Schuette | 128/2.05 |
| 3,882,861 | 5/1975 | Kettering et al. | 128/214 |
| 3,982,535 | 9/1976 | Bahrton | 128/214 |
| 4,060,485 | 11/1977 | Eaton | 210/87 |
| 4,080,966 | 3/1978 | McNally et al. | 128/214 |
| 4,148,314 | 4/1979 | Yin | 128/214 |
| 4,231,366 | 11/1980 | Schael | 128/214 |
| 4,309,993 | 1/1982 | Brown | 128/214 |
| 4,373,525 | 2/1983 | Kobayashi | 128/214 |
| 4,444,546 | 4/1984 | Pazemenas | 417/12 |
| 4,447,191 | 5/1984 | Bilstad et al. | 417/12 |
| 4,460,353 | 7/1984 | Deckert et al. | 604/31 |
| 4,589,822 | 5/1986 | Clausen et al. | 415/170 |
| 4,606,698 | 8/1986 | Clausen et al. | 415/170 |
| 4,643,641 | 2/1987 | Clausen et al. | 415/170 |
| 4,690,002 | 9/1987 | Hubbard et al. | 73/861.25 |
| 4,778,445 | 10/1988 | Hubbard et al. | 604/4 |
| 4,781,525 | 11/1988 | Hubbard et al. | 415/30 |
| 4,863,425 | 9/1989 | Slate et al. | 604/65 |
| 4,984,972 | 1/1991 | Clausen et al. | 417/420 |
| 4,989,609 | 2/1991 | Smith et al. | 128/661.08 |
| 4,993,418 | 2/1991 | Weaver et al. | 128/661.08 |

FOREIGN PATENT DOCUMENTS 0378251 7/1990 European Pat. Off. .

OTHER PUBLICATIONS

Tsutsui et al.; "Idioperipheral Pulsation During Non-pulsatile Biventricular Bypass Experiments", A.S.A.I.O. Transactions, vol. 32, No. 1, Jul. 1986, pp. 263-268.

Primary Examiner—William H. Grieb
Assistant Examiner—Steven B. Wong
Attorney, Agent, or Firm—Gary L. Griswold; Walter N. Kirn; Stephen W. Bauer

[57] ABSTRACT

A blood pumping system with a non-occlusive blood pump has a backflow warning generator to generate a warning to indicate that undesirable backflow of blood through the non-occlusive blood pump may be impending. The backflow warning generator comprises a microprocessor that executes a backflow alert routine that generates a backflow warning when one of two sets of conditions is satisfied. The first set of conditions tests for the presence of an average blood flow change rate within predetermined limits, an average blood flow within predetermined limits, and a change in the operating speed of the non-occlusive pump. the second set of conditions tests for the presence of an average blood flow greater than zero, a previous RPM value greater than a specified constant, and a current RPM value less than the specified constant.

26 Claims, 3 Drawing Sheets

BLOOD PUMPING SYSTEM WITH BACKFLOW WARNING

BACKGROUND OF THE INVENTION

The present invention relates to a blood pumping system having a particular manner of generating a backflow warning to warn of blood backflow through a non-occlusive blood pump.

Blood pumping systems are used in clinical situations, such as open-heart surgery, to provide blood circulation for the patient undergoing the surgery. A typical blood pumping system draws blood from a patient's venous system into an external conduit connected to the inlet of a blood pump. The blood is pumped into to the patient's arterial system via a second conduit connected to the outlet of the blood pump. The first and/or second conduit may be connected to other devices to provide blood filtering, heating, oxygenation, collection, etc.

While various types of blood pumps have been used in blood pumping systems, one particular type of pump that has been found to be generally advantageous is a centrifugal pump. Such a pump is described in U.S. Pat. No. 4,589,822 to Clausen, et al. One characteristic of centrifugal blood pumps is that they are "non-occlusive," which means that when connected to a conduit, the mechanical structure of the pump allows blood to flow in the direction opposite the blood pumping direction. As a result, even though a non-occlusive blood pump may be turned on and operating, blood may actually flow backwards through the pump in the wrong direction, which may have adverse consequences for the patient.

As is known, the primary adverse effect of such backflow is that air may be drawn into the blood within the pumping system and pumped into the patient when the blood flow is later reversed to the proper direction. If the perfusionist or doctor detects that air has been drawn into the pumping system, there are procedures to prevent the air from being pumped into the patient. However, these procedures are tedious and/or time-consuming. Moreover, the perfusionist or doctor may not notice that air has been drawn into the system.

Backflow occurs when the output pressure of the blood pump is exceeded by the load pressure of the patient. This load pressure depends on such factors as the resistance of the arterial and venous systems of the patient, which may vary with the physical size and age of the patient; the resistance of the external pumping system; the relative elevation of the patient with respect to the blood pumping system; etc. If for any reason the load pressure should happen to exceed the output pressure of the pump, backflow will occur.

One blood pumping system that generates a warning that backflow is taking place is disclosed in U.S. Pat. No. 4,778,445 to Hubbard, et al. In that system, the blood flow from a centrifugal pump into the patient is sensed by a non-directional flow sensor. The speed, in RPMs, of a motor connected to drive the pump is also sensed. Generally, the Hubbard, et al. system determines when there is backflow by comparing the change in the actual flow over time with the change in the motor speed over time. For example, if the magnitude of the blood flow to the patient increases in response to an increase in the motor RPM rate, the blood flow is assumed to be into the patient. However, if the magnitude of the blood flow decreases in response to an increase in the motor RPM rate, it is assumed that there is backflow, and an appropriate warning is generated.

SUMMARY OF THE INVENTION

The present invention is directed to a blood pumping system in which a non-occlusive blood pump is used. The blood pumping system includes a pair of conduits connected to a patient. One of the conduits supplies blood from the venous system of the patient to the inlet of the non-occlusive blood pump, and the other conduit supplies blood from the outlet of the blood pump to the arterial system of the patient. A blood oxygenator and/or other equipment may optionally be used to oxygenate the blood and perform other functions.

The blood pumping system includes a backflow warning generator that is capable of generating a warning, which may be an alert or an alarm, that warns the operator of the blood pumping system, or perfusionist, of backflow or impending backflow. The backflow warning generator causes alerts to be generated in response to sensing various conditions within the blood pumping system. These conditions include the following: 1) the rate at which the blood flow is changing within the system; 2) the magnitude of the blood flow within the system; 3) whether the operating speed of the blood pump has changed; and 4) the absolute operating speed of the blood pump.

The blood pumping system generates backflow alerts prior to actual backflow within the system, thus allowing the perfusionist the opportunity to attempt to avoid the occurrence of actual backflow by such actions as clamping one of the conduits in the blood pumping system or increasing the speed at which the blood pump is operating. The manner in which the backflow alerts are generated is advantageous in that they are generated in situations in which backflow is impending or imminent, but not in situations in which backflow is not actually impending.

These and other features and advantages of the present invention will be apparent to those of ordinary skill in the art in view of the detailed description of the preferred embodiment, which is made with reference to the drawings, a brief description of which is provided below.

DETAILED DESCRIPTION OF A PREFERRED EMBODIMENT

Figure 1:
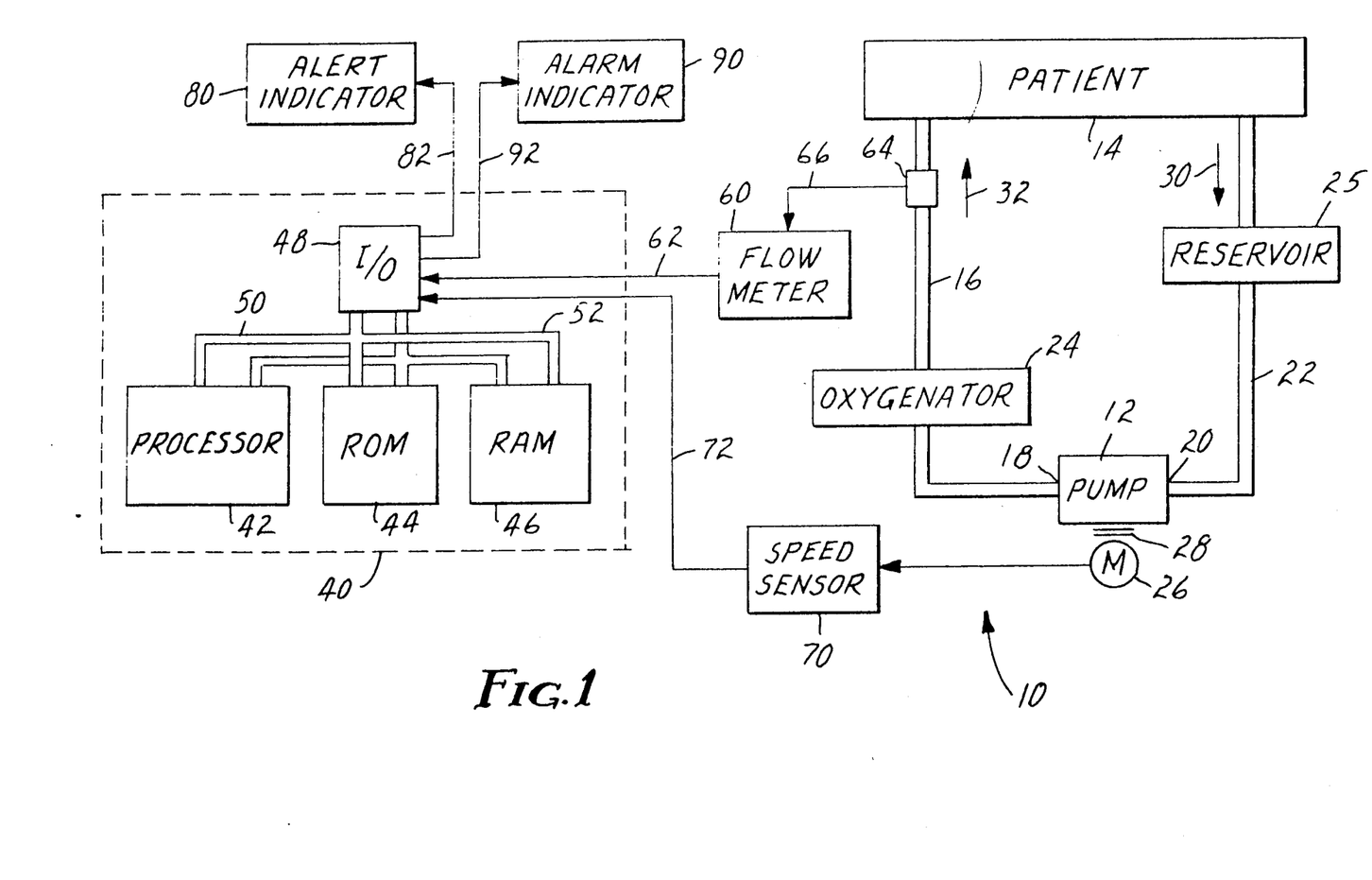
FIG. 1 is a schematic diagram of a blood pumping system in accordance with a preferred embodiment of the invention.

A preferred embodiment of a blood pumping system 10 is shown in FIG. 1. The blood pumping system 10 includes a non-occlusive blood pump 12 connected to the arterial system of a patient 14 via a conduit 16 connected to the outlet 18 of the pump 12. The inlet 20 of the pump 12 is connected to a conduit 22 that is connected to the venous system of the patient 14. A blood oxygenator 24 is connected to the conduit 16 to oxygenate the blood, and a reservoir 25 is connected to the conduit 22 to temporarily store excess blood.

The pump 12 is driven by a motor 26 coupled to the pump 12 via magnetic coupling means 28. The pump 12 may be any type of non-occlusive pump, such as centrifugal pumps of the type disclosed in U.S. Pat. Nos. 4,589,822 and 4,984,972 to Clausen, et al., the disclosures of which are incorporated herein by reference.

In operation, blood is supplied from the patient 14 to the inlet 20 of the pump 12 via the conduit 22 in the direction of the arrow 30. The blood is pumped from the outlet 18 of the pump 12, through the oxygenator 24, and then to the arterial system of the patient via the conduit 16 in the direction of the arrow 32.

The blood pumping system 10 also includes a backflow warning generator 40 to generate backflow alerts and alarms. As used herein, the term "alert" refers to a warning that backflow is not yet present but may be impending, and the term "alarm" refers to a warning that there is actual backflow. Thus, a backflow alert warns of impending backflow prior to the existence of actual backflow.

The backflow warning generator 40 includes a microprocessor 42, a read-only memory (ROM) 44, a random-access memory (RAM) 46, and an input/output (I/O) circuit 48 which are interconnected by an address bus 50 and a data bus 52. The I/O circuit 48 may be any conventional type of I/O circuit such as a bank of bidirectional buffers, a universal asynchronous receiver/transmitter (UART), etc.

The I/O circuit 48 is connected to receive a signal indicative of the blood flow through the conduit 16 from a flow measurement device 60, such as a flow meter, via a line 62. The flow meter 60 is connected to a flow sensor 64 via a line 66.

The sensed blood flow through the conduit 16 will at all times be substantially the same as the blood flow through the pump 12. Thus, if there is backflow through the conduit 16 there will be backflow through the pump 12.

The flow measurement system 60, 64 may be any type of system or device that is capable of generating a signal indicative of the blood flow, and is referred to herein as a "flow sensor." One example of a flow sensor that could be used is disclosed in U.S. Pat. No. 4,690,002 to Hubbard, et al., the disclosure of which is incorporated herein by reference. The specific type of flow sensor used is not germane to the present invention.

Moreover, the benefits of the invention may be achieved without using a flow sensor at all. In this case, the magnitude of blood flow through the conduit 16 could be determined indirectly based upon the RPM rate and torque of the motor 26. A system that measures flow rate indirectly in this manner is described in U.S. Pat. No. 4,781,525 to Hubbard, et al., the disclosure of which is incorporated herein by reference.

The I/O circuit 48 is also connected to receive a signal indicative of the speed of the pump 12. This signal is generated by a speed sensor 70 connected to the motor 26 and is transmitted to the I/O circuit 48 via a line 72. Although the speed sensor 70 is schematically shown to be separate from the motor 26, the speed sensor 70 is actually provided integrally with the motor 26 and comprises a plurality of Hall-effect sensors coupled to sense the speed of rotation of the magnets within the motor 26. If a speed sensor is used to sense the speed of the pump 12, any type of speed sensor could be provided.

Moreover, the speed of the pump 12 could be determined without use of a speed sensor or similar device. For example, if the speed of the pump 12 is set by a potentiometer connected to a rotary dial set by the operator of the blood pumping system 10, or "perfusionist," the pump speed could be obtained simply by reading the voltage provided by the potentiometer.

In response to receiving the signals indicative of the magnitude of blood flow through the conduit 16 and the speed of the pump 12 via the lines 62 and 72, respectively, the backflow warning generator 40 determines whether the condition of the blood pumping system justifies the generation of either a backflow alert, in the case of impending backflow, or a backflow alarm, in the case of actual backflow. If there is a backflow alert condition, the I/O circuit 48 transmits a signal to an alert indicator 80 via a line 82 to generate the backflow alert. If there is a backflow alarm condition, the I/O circuit 48 transmits a signal to an alarm indicator 90 via a line 92 to generate the backflow alarm.

The backflow alert and backflow alarm may be any type of visual or audio alarms such as flashing lights or buzzers. It is preferable that these two warnings be distinguishable so that the perfusionist can easily distinguish between the backflow alert and the backflow alarm. It may happen that both the backflow alert and alarm are activated at substantially the same time. In this case, it may be advantageous to activate only the backflow alarm and override the backflow alert.

The present invention relates to the particular manner in which the backflow alert is generated, and the benefits of the invention may be achieved without the use of a backflow alarm.

With respect to the backflow alarm, that alarm could be generated in any number of ways, including, for example, in accordance with U.S. Pat. No. 4,778,445 to Hubbard, et al., the disclosure of which is incorporated herein by reference, or where a directional flow sensor is used, simply by generating the alarm when the direction of blood flow is reversed.

BACKFLOW ALERT ROUTINE

Figure 2A:
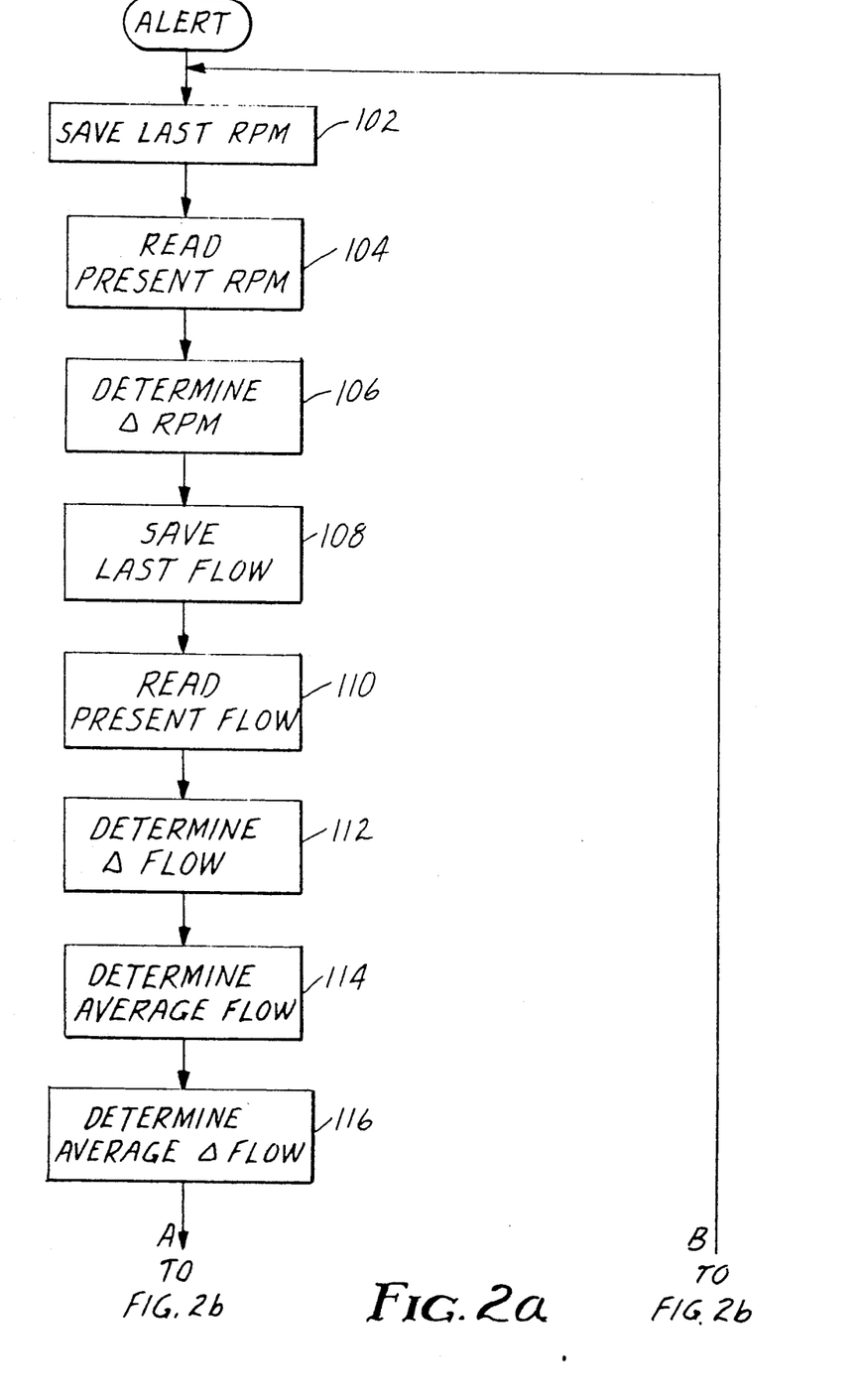
FIGS. 2a and 2b are a flowchart of a backflow alert routine stored in the ROM and executed by the microprocessor of FIG. 1.
Figure 2B:
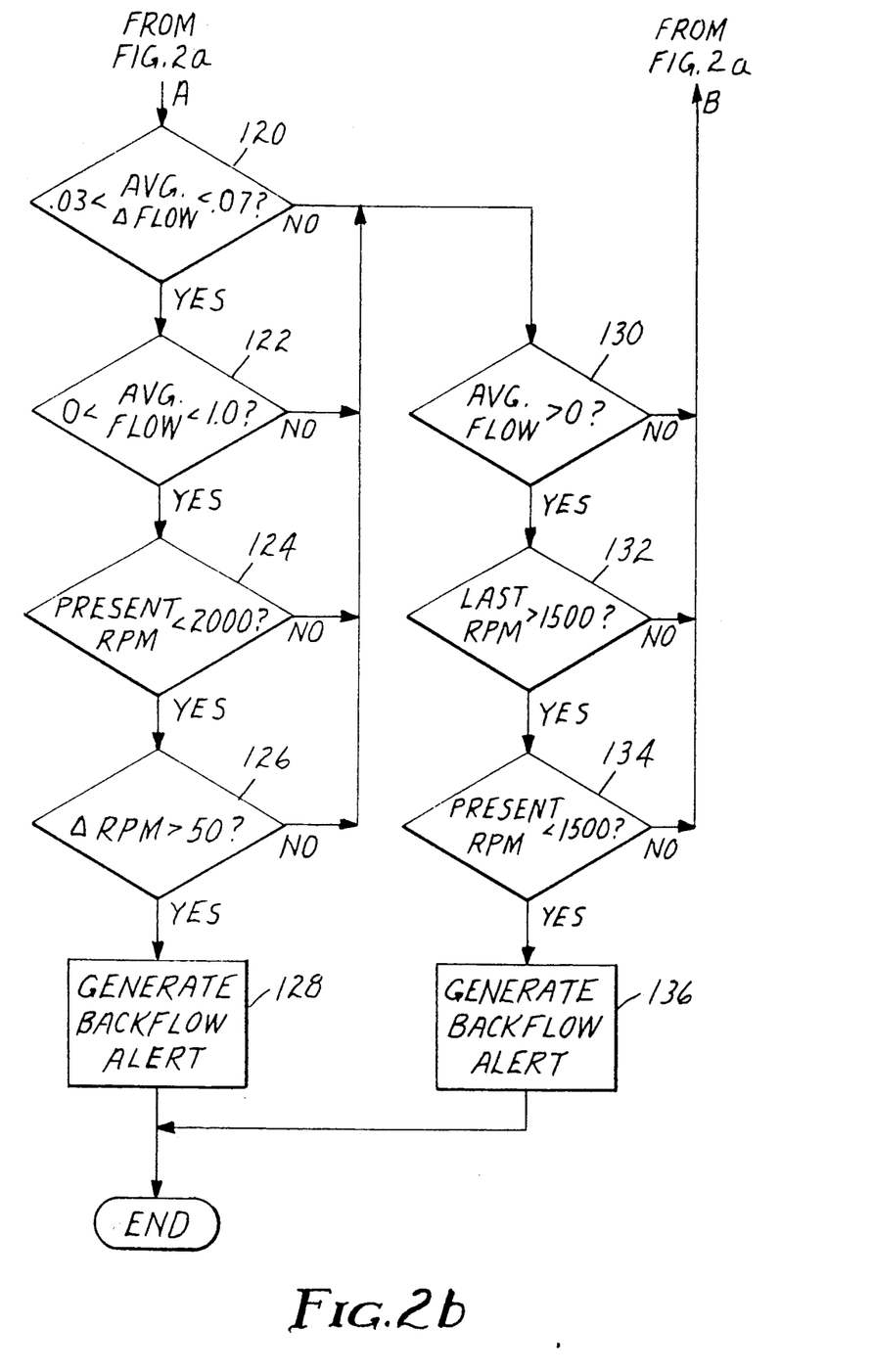

The manner in which backflow alerts are generated is controlled by a portion of a computer program stored in the ROM 44 and executed by the microprocessor 42 referred to herein as a backflow alert routine. A flowchart of the backflow alert routine is shown in FIGS. 2a and 2b. The backflow alert routine is described below in general, and then its operation is described in connection with a number of various scenarios that may occur during a clinical situation, such as open heart surgery.

The backflow alert routine generates a backflow alert in certain cases based upon the following factors: 1) the rate at which the blood flow through the pump 12 is changing, as determined by calculating an average of a number of successive blood flow changes through the conduit 16; 2) the magnitude of the blood flow through the system, as determined by calculating the average blood flow through the conduit 16; 3) whether the operating speed of the pump has changed, as determined by taking two successive RPM measurements of the motor 26; and 4) the operating speed of the pump 12 as measured by the RPM rate of the motor 26.

The backflow alert routine is periodically executed to continually check for the presence of an undesirable backflow condition. In the preferred embodiment, the routine is executed three times per second. Of course, other rates of execution could be used.

Referring to FIG. 2a, the backflow alert routine begins execution at step 102, where the last value of the RPM value of the motor 26 is saved in memory. At step 104, the present RPM value of the motor 26 is determined by reading the RPM signal provided by the speed sensor 70 to the I/O circuit 48 via the line 72. At step 106, the change in RPM from the last value stored at step 102 and the present value read at step 104 is determined and stored in memory.

At step 108, the magnitude of the last blood flow rate is saved in memory. At step 110, the magnitude of the present blood flow rate through the conduit 16 is determined by reading the flow rate signal generated by the flow meter 60 and provided to the I/O circuit 48 via the line 62. At step 112, the change in the blood flow rate through the conduit 16 is determined by calculating the difference between the present flow rate read at step 110 and the previous flow rate stored in memory at step 108.

At step 114, the average blood flow through the conduit 16 is determined based upon a predetermined number of prior readings of the flow rate that were taken during prior executions of step 110. For example, 10 successive flow rate readings may be used to generate the flow rate average. Of course, the number of flow rate readings used in the determination of the average flow rate will affect the sensitivity of the flow rate average to instantaneous changes in the flow rate. Thus, a given change in the flow rate will affect a flow rate average based on 10 readings more than it will affect an average based on 100 readings. In the preferred embodiment, six flow readings are used to generate the average flow rate.

At step 116, the average rate of blood flow change is determined by calculating the average of a predetermined number of flow rate changes determined during prior executions of step 112. The sensitivity of this average will also depend on the number of data samples used to generate the average. In the preferred embodiment, five flow rate change data samples are used to generate this average.

While the description of FIG. 2b below refers to specific numeric values, it should be appreciated that the invention is not limited to such values. The specific values are used by way of example only to aid in the explanation of the invention. The specific values used may vary depending upon the patient, the hospital in which the backflow system is used, the particular non-occlusive pump used in the system, etc.

Now referring to FIG. 2b, a backflow alert will be generated if each condition in either of two sets of conditions is satisfied. Steps 120-126 shown in the right-hand portion of FIG. 2b test for the presence of one set of conditions, and steps 130-134 shown in the left-hand portion of FIG. 2b test for the second set of conditions. If all conditions in either set of conditions is satisfied, a backflow alert is generated.

Steps 120-126 check for the presence of each condition in the first set. At step 120, the magnitude of the average rate of change in the blood flow, or blood flow change rate, that was determined in step 116 is tested to determine whether it is within a predetermined numeric range. The upper range limit is shown in FIG. 2b to be 0.07, which represents liters-per-minute/second (LPM/s), and the lower range limit is shown to be 0.03 LPM/s.

The lower limit of 0.03 LPM/s is intended as a change rate threshold that must be surpassed before a backflow alert will be generated. Any average flow change rates of less than 0.03 LPM/s do not represent substantial changes that may be cause for concern. Thus, if the average flow change rate is less than 0.03 LPM/s, the first condition being tested for fails and the program branches to step 130 to determine whether each condition in the second set of conditions is satisfied.

The upper limit of 0.07 LPM/s in step 120 is intended to prevent the generation of a backflow alert in certain cases, for example, where the conduit 16 is clamped. The conduit 16 may be purposely clamped several times during a clinical procedure for various reasons. When the conduit 16 is clamped, the flow through it immediately becomes zero, resulting in a very large average blood flow change rate, higher than 0.07 LPM/s. Since it is undesirable to generate a backflow alert in normal circumstances, when step 120 is performed in this case, the first set of conditions will fail, and the program will branch to step 130.

If the average flow change rate is within the upper and lower limits of step 120, the program branches to step 122 where the magnitude of the average blood flow is tested to determine whether it is less than 1.0 LPM. The normal blood flow through a person is on the order of 3-5 LPM. The 1.0 LPM value of step 122 is used to more or less arbitrarily define what is considered to be a low blood flow. If the average blood flow is greater than 1.0 LPM, the blood flow is not considered to be low, and thus it is assumed that backflow is not imminent. Accordingly, in that case the first set of conditions fails and the program branches to step 130 where the program determines whether the second set of conditions is present.

If the average blood flow was less than 1.0 LPM as determined at step 122, the program branches to step 124 where the present RPM value of the motor 26 is tested to determine whether it is less than 2,000.

Step 124 is used to reduce the likelihood that spurious alerts are generated. In particular, if the present RPM value is greater than 2,000, which would usually cause a relatively high blood flow to be provided, a backflow alert is not generated.

If the present RPM value is less than 2,000, the program branches to step 126 where the change in successive RPM values as determined at step 106 is tested to determine whether it is greater than 50. The 50 RPM value is used as a minimum threshold to define when the speed of the motor 26 driving the pump 12 is changed by the perfusionist. During normal operation, at constant pump speed, there are relatively small fluctuations in the pump speed as sensed by the speed sensor 70, even though the perfusionist did not change the pump speed. These expected fluctuations in the RPM value do not trigger an RPM change since their magnitude is less than 50.

If there was an RPM change greater than 50, thus indicating that the perfusionist changed the RPM setting of the motor 26, the final condition in the first set of conditions is satisfied, and the program branches to step 128 where the backflow alert is generated. If the RPM change was less than 50 RPM, the program branches to step 130 to determine whether the second set of conditions is satisfied.

Steps 130-134 test for the presence of each condition in the second set of conditions. At step 130, the average blood flow determined at step 114 is tested to determine whether it is nonzero, which in this case is tested by determining whether it is greater than zero. If the average blood flow is zero, that is an indication that the conduit 16 has been clamped by the perfusionist, which as described above is an intentional act that should not generate a backflow alert. Thus, if the average blood flow is zero, the second set of conditions fails, and the program branches back to step 102 in FIG. 2a to repeat the backflow alert routine.

If the average blood flow is greater than zero as determined at step 130, the program branches to step 132. Steps 132 and 134 together determine whether the RPM value has changed in a certain manner. In particular, steps 132 and 134 together test whether the RPM value has been reduced from an initial value above 1,500 RPM to a later value of less than 1,500 RPM.

At step 132, the last RPM value stored in memory at step 102 is tested to determine whether it is greater than 1,500. If it is, the program branches to step 134 where the present RPM value is tested to determine whether it is less than 1,500. The particular value of 1,500 represents a minimum RPM value that would generate a relatively low flow close to zero flow. If the present RPM value is less than 1,500, the program branches to step 136 where the backflow alert is generated.

REAL ALERT SCENARIOS

An advantage in the design of the backflow alert routine just described is its ability to distinguish real backflow alert scenarios from "spurious" backflow alert scenarios. This ability minimizes or eliminates any false alerts that otherwise might be generated by the system, while at the same time ensuring that all or most situations in which backflow is truly impending or imminent cause an alert to be generated.

In order to more fully appreciate the advantageous manner in which the backflow alert is generated in accordance with the flowchart of FIGS. 2a and 2b, one should understand a number of various scenarios that may occur during a clinical situation, such as open heart surgery. The scenarios described below include both real alert scenarios which should result in the generation of a backflow alert as well as spurious alert scenarios which should not result in the generation of a backflow alert.

The particular scenarios described below are provided only to aid in understanding the invention and are not intended to represent all possible scenarios that could occur during a clinical situation or all scenarios for which the present invention was designed to take into account.

One real alert scenario which should result in the generation of a backflow alert occurs when the perfusionist rapidly decreases the blood flow to the patient. Rapidly decreasing the blood flow is routinely done, for example, prior to draining the heart where a bypass procedure is to be performed.

Where an occlusive pump such as a roller pump is being used, the blood flow is rapidly decreased simply by quickly reducing the RPM setting of the pump motor. Undertaking this action will not cause backflow because an occlusive pump is being used.

However, if a non-occlusive pump is being used, the perfusionist should be careful not to reduce the RPM setting below a predetermined minimum value, since that would result in backflow. If the perfusionist does turn down the RPM setting below the minimum setting, a backflow alert is generated.

Referring to FIG. 2b, the manner in which the backflow alert is generated is as follows. The backflow alert routine would reach step 120 after performing the steps 102–116 to determine the appropriate flow values. At step 120, the average blood flow change rate would be larger than 0.07 LPM/s since the RPM setting was changed very quickly by the perfusionist. The program would thus branch to step 130, where the average flow would still be greater than zero since all the previous flow values used to calculate the average flow would be greater than zero. The program would thus branch to step 132, where the last RPM value would be checked to determine whether it was greater than 1,500. This would be the case since the 1,500 RPM value represents very low flow, and since the pump RPM setting prior to turning the RPM down was selected to deliver normal blood flow. As a result, the program would branch to step 134, where the present RPM value would be found to be less than 1,500 since the perfusionist turned the RPM setting to a low setting. A backflow alert would thus result at step 136.

A second real alert scenario would be where the perfusionist changes the RPM setting of the motor 26 relatively slowly in order to decrease the blood flow to the patient. While this action by the perfusionist is intended and usually does not generate a backflow alert condition, if the RPM setting is reduced too much, backflow may be impending, and an alert is generated in this case.

Referring to FIG. 2b, the alert would be generated as follows. At step 120, the average flow change rate would fall within the specified range since there is significant flow rate change and since the flow change is less than the maximum value because the perfusionist turned down the RPM setting relatively slowly. The program would thus branch to step 122.

At step 122, the average flow would be less than 1.0 LPM since that is the number chosen to define low flow. It should be understood that the backflow alert routine might be executed several times before the average flow drops below the upper limit. That would depend, for example, on the number of data samples used to calculate the flow average. The average flow would be larger than the lower limit of 0 LPM since there would still be blood flow. Thus, the program would branch to step 124.

Step 124 would be satisfied since the present RPM value was below 2,000 RPM. This would be the case since RPM values greater than 2,000 generally yield substantially greater flows than 1.0 LPM. Step 126 would be satisfied since there was an actual RPM change, and thus the backflow alert would be generated at step 128.

SPURIOUS ALERT SCENARIOS

There are also a number of spurious alert scenarios that should not result in the generation of a backflow alert since backflow is not impending in these situations.

One such scenario is where the perfusionist clamps the conduit 16 without changing the RPM setting of the motor 26. In this case, since the conduit was clamped, no backflow through the pump 12 occurs, and thus no backflow alert is generated.

Referring to FIG. 2b, there are a number of steps in the backflow routine that prevent the generation of a backflow alert in this case. The backflow alert will not be generated via steps 120–128 since step 126 requires that there be a change in the RPM value and also because the upper range limit of 0.07 LPM/s in step 120 would be exceeded due to the fast rate of flow change cause by the flow becoming immediately zero. The alert will not be generated via steps 130–136 since steps 132 and 134 together require a change in the RPM value.

Another spurious alert scenario is if the perfusionist clamps the conduit 16 and then several seconds later turns the RPM setting of the motor 26 to zero. This would normally occur at or near the end of the clinical procedure. This spurious scenario does not generate a backflow alert because by the time that the RPM setting was changed to zero, the average blood flow drops to zero.

Referring again to FIG. 2b, in this case a backflow alert is not generated by steps 120-128 since the average flow is zero as determined at step 122 before there is any change in the RPM value as determined at step 126. Similarly, the backflow alert is not generated by steps 130-136 since the average flow is zero as determined at step 130 before there is any RPM change as determined at steps 132 and 134.

A third spurious alert scenario may occur where the perfusionist removes the flow sensor 64 from the conduit 16. This may be done, for example, to reposition the flow sensor 64 to a new location on the conduit 16. In this case, the RPM setting of the motor 26 will not normally be changed. When the flow sensor 64 is removed from the conduit 16, the flow signal immediately indicates zero flow.

No backflow alert in this case is generated by steps 120-128 since step 126 requires an RPM change and also since the upper limit of 0.07 LPM/s in step 120 would be exceeded due to the fast rate of flow change. No alert is generated by steps 130-136 since steps 132 and 134 together require an RPM change.

It should be understood that the above description of the specific operation of the backflow alert routine for each of the real and spurious alert scenarios is intended only to aid in understanding the invention. The backflow alert routine may operate differently for the above scenarios under certain circumstances, for example, if different high and low threshold values and/or RPM thresholds are used. The number of data samples used to determine the average flow and the average flow rate change could also affect the specific operation of the alert routine.

Many modifications and alternative embodiments of the invention will be apparent to those of ordinary skill in the art in view of the foregoing description of the preferred embodiment. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A blood pumping system having a backflow warning system that generates a warning of impending backflow of blood through a non-occlusive blood pump, said blood pumping system comprising:
    a non-occlusive blood pump having an inlet and an outlet, said blood pump pumping blood from said inlet to said outlet;
    a first conduit connected to said inlet of said blood pump, said first conduit being connectable to a patient so as to enable blood flow to said inlet of said blood pump;
    a second conduit connected to said outlet of said blood pump, said second conduit being connectable to a patient so as to enable blood flow from said outlet of said blood pump to the patient;
    first means for generating a signal indicative of the magnitude of the blood flow through said blood pumping system;
    second means for generating a signal indicative of the speed of said blood pump; and
    a backflow warning generator coupled to said first and second means that causes a backflow warning to be generated in response to the rate of change of blood flow rising above a threshold value, the backflow warning generator including means for determining the rate of change of blood flow from signals generated by the first means at different times.

2. A blood pumping system as defined in claim 1 additionally comprising a motor coupled to said non-occlusive blood pump and wherein said second means generates said signal indicative of the speed of said blood pump by sensing the RPM rate of said motor.

3. A blood pumping system as defined in claim 1 wherein said first means comprises a flow sensor coupled to one of said first and second conduits.

4. A blood pumping system as defined in claim 1 wherein said backflow warning is generated prior to actual backflow of blood through said non-occlusive blood pump.

5. A blood pumping system as defined in claim 1 wherein said backflow warning generator comprises a programmed microprocessor.

6. A blood pumping system as defined in claim 1 wherein said backflow warning generator generates said backflow warning additionally in response to the magnitude of the blood flow falling below a threshold value.

7. A blood pumping system as defined in claim 6 wherein said backflow warning generator generates said backflow warning in response to the average magnitude of the blood flow falling below said threshold value.

8. A blood pumping system as defined in claim 1 wherein said backflow warning generator does not generate said backflow warning when the speed of said non-occlusive blood pump has not substantially changed.

9. A blood pumping system as defined in claim 1 wherein said backflow warning generator generates said backflow warning in response to the average rate of change of blood flow rising above said threshold value.

10. A blood pumping system as defined in claim 1 wherein said backflow warning generator generates said backflow warning in response to the average rate of change of blood flow rising above a first threshold value constituting said threshold value but not above a second threshold value having a magnitude greater than said first threshold value.

11. A method of generating a backflow warning of impending backflow in a blood pumping system having a non-occlusive blood pump, said method comprising the steps of:
    (a) generating a signal indicative of the magnitude of blood flow through the blood pumping system;
    (b) comparing the magnitude of the blood flow with a threshold value; and
    (c) generating a backflow warning in response to the magnitude of the blood flow falling below the threshold value as determined in said step (b).

12. A method as defined in claim 11 additionally comprising the step of:

(d) determining whether the speed at which the non-occlusive pump is operating has substantially changed, and wherein the backflow warning is generated only when the speed of the non-occlusive blood pump has substantially changed as determined in said step (d).

13. A method as defined in claim 11 additionally comprising the steps of:
(d) repeating said step (a) to generate a second signal indicative of the magnitude of the blood flow through the blood pumping system;
(e) determining an average blood flow magnitude based upon the signal generated in said step (a) and the second signal generated in said step (d),
wherein the blood flow magnitude of said step (b) is the average blood flow magnitude determined in said step (e); and
wherein during said step (c) the backflow warning is generated in response to the average blood flow magnitude falling below the threshold value.

14. A method as defined in claim 11 wherein the backflow warning is generated prior to actual backflow of blood through said non-occlusive blood pump.

15. A method of generating a backflow warning in a blood pumping system having a non-occlusive blood pump, said method comprising the steps of:
(a) generating a first signal indicative of the magnitude of blood flow through a non-occlusive pump at a first time;
(b) generating a second signal indicative of the magnitude of blood flow through the non-occlusive blood pump at a second time;
(c) determining an average blood flow through the non-occlusive blood pump;
(d) determining the speed at which the non-occlusive blood pump is operating; and
(e) generating a backflow warning based upon the average blood flow through the non-occlusive blood pump as determined in said step (c) and the speed at which the blood pump is operating as determined in said step (d).

16. A method as defined in claim 15 wherein the first and second signals indicative of the magnitude of the blood flow in said steps (a) and (b) are generated by a flow sensor.

17. A method as defined in claim 15 wherein the backflow warning is generated in response to the average blood flow being nonzero and the operating speed of the blood pump being lower than a threshold value.

18. A method as defined in claim 15 additionally comprising the steps of:
(f) determining a blood flow change by determining the difference between the flow indicated by the first signal in said step (a) and the flow indicated by the second signal in said step (b);
(g) repeating said step (f) to generate a second blood flow change;
(h) determining an average rate of blood flow change based upon the blood flow change determined in said step (f) and the second blood flow change determined in said step (g),
and wherein the backflow warning generated in said step (e) is additionally based upon the average rate of blood flow change determined in said step (h).

19. A method as defined in claim 15 additionally comprising the steps of:

(f) repeating said step (d) at a different time to make a second determination of the speed at which the non-occlusive pump is operating; and
(g) determining the change in operating speed of the pump based upon the difference between the pump speed as determined in said step (d) and the pump speed as determined in said step (f),
and wherein the backflow warning generated during said step (e) is additionally based on the change in operating speed of the pump determined in said step (g).

20. A method as defined in claim 15 wherein the backflow warning is generated prior to actual backflow of blood through said non-occlusive blood pump.

21. A method as defined in claim 15 additionally comprising the steps of:
(f) determining a blood flow change by determining the difference between the flow indicated by said first signal in said step (a) and the flow indicated by said second signal in said step (b);
(g) repeating said step (f) to generate a second blood flow change;
(h) determining an average rate of blood flow change based upon the blood flow change determined in said step (f) and the second blood flow change determined in said step (g),
(i) repeating said step (d) at a different time to make a second determination of the speed at which the non-occlusive pump is operating; and
(j) determining the change in operating speed of the pump based upon the difference between the pump speed as determined in said step (d) and the pump speed as determined in said step (i),
and wherein the backflow warning generated in said step (e) is additionally based on the change in operating speed of the pump determined in said step (j) and the average rate of blood flow change determined in said step (h).

22. A method as defined in claim 15 additionally comprising the steps of:
(f) repeating step (d) at a different time to make a second determination of the speed at which the non-occlusive pump is operating; and
(g) determining whether the operating speed of the pump as defined in said steps (f) is on the opposite side of a predetermined speed threshold value from the operating speed of the pump as determined in said step (d);
and wherein the backflow warning is generated in response to a determination in said (g) that the operating speeds of the pump determined in said steps (d) and (f) are on opposite sides of the predetermined speed threshold value.

23. A method as defined in claim 15 additionally comprising the steps of:
(f) repeating step (d) at a different time to make a second determination of the speed at which the non-occlusive pump is operating;
(g) determining whether the operating speed of the pump as determined in said step (d) is above a predetermined speed threshold value;
(h) determining whether the operating speed of the pump as determined in said step (f) is below the predetermined speed threshold value;
and wherein the backflow warning is generated in response to determinations in said steps (g) and (h) that the operating speed of the pump determined in step (d) is above the predetermined speed threshold value and the operating speed of the pump determined in said step (f) is below the predetermined speed threshold value.

24. A method of generating a backflow warning in a blood pumping system having a non-occlusive blood pump, said method comprising the steps of:
(a) determining the speed at which the non-occlusive blood pump is operating to make a first determination of the operating speed of the pump at a first time;
(b) repeating said step (a) at a different time to make a second determination of the operating speed of the pump at a second time;
(c) determining whether the operating speed of the pump as determined in said step (a) is above a predetermined speed threshold value;
(d) determining whether the operating speed of the pump as determined in said step (b) is below the predetermined speed threshold value; and
(e) generating a backflow warning in response to determinations in steps (c) and (d) that the operating speed of the pump determined in said step (a) is above the predetermined speed threshold value and the operating speed of the pumping determined in said step (b) is below the predetermined speed threshold value.

25. A method as defined in claim 24 additionally comprising the steps of:
(f) determining whether blood flow through the pump is nonzero;
and wherein the backflow warning generated in said step (e) is additionally based upon the blood flow as determined in said step (f) being nonzero.

26. A method as defined in claim 24 additionally comprising the steps of:
(f) determining whether average blood flow through the pump is nonzero;
and wherein the backflow warning generated in said step (e) is additionally based upon the average blood flow as determined in said step (f) being nonzero.

* * * * *